United States Patent
Phisitkul et al.

(10) Patent No.: US 10,842,480 B2
(45) Date of Patent: Nov. 24, 2020

(54) MULTIPLE SUTURE THREADER AND METHODS OF USE

(71) Applicant: Crossroads Extremity Systems, LLC, Memphis, TN (US)

(72) Inventors: Phinit Phisitkul, Coralville, IA (US); Justin Taber, Honolulu, HI (US); T. Wade Fallin, Hyde Park, UT (US)

(73) Assignee: CROSSROADS EXTREMITY SYSTEMS, LLC, Memphis, TN (US)

( * ) Notice: Subject to any disclaimer, the term of this patent is extended or adjusted under 35 U.S.C. 154(b) by 340 days.

(21) Appl. No.: 15/641,618

(22) Filed: Jul. 5, 2017

(65) Prior Publication Data

US 2018/0008258 A1 Jan. 11, 2018

Related U.S. Application Data

(60) Provisional application No. 62/358,231, filed on Jul. 5, 2016, provisional application No. 62/425,560, filed
(Continued)

(51) Int. Cl.
*A61B 17/04* (2006.01)
*A61B 17/06* (2006.01)
(Continued)

(52) U.S. Cl.
CPC ...... *A61B 17/0401* (2013.01); *A61B 17/0485* (2013.01); *A61B 17/06166* (2013.01);
(Continued)

(58) Field of Classification Search
CPC ...... A61B 17/0485; A61B 2017/06023; A61B 2017/0498; A61B 17/0482; A61B 17/0483; A61B 17/32056
See application file for complete search history.

(56) References Cited

U.S. PATENT DOCUMENTS

| 2,181,746 A | 11/1939 | Siebrandt |
| 2,291,413 A | 7/1942 | Siebrandt |
(Continued)

FOREIGN PATENT DOCUMENTS

| CA | 551446 A | 1/1958 |
| EP | 132284 A1 | 1/1985 |
(Continued)

OTHER PUBLICATIONS

International Search Report and Written Opinion for Int. Appl. No. PCT/US2017/064173 dated Feb. 14, 2018, 8 pp.
(Continued)

*Primary Examiner* — Shaun L David
*Assistant Examiner* — Christina C Lauer
(74) *Attorney, Agent, or Firm* — David Meibos; Maywood IP Law

(57) ABSTRACT

The disclosure provides apparatus and methods of use pertaining to a multiple suture threader. Embodiments of the multiple suture threader include a handle that is coupled with a first collapsible loop and a second collapsible loop that is axially offset from the first collapsible loop. In use, one or more sutures are doubled over each of the first and the second collapsible loops such that when the axially spaced loops are passed through a narrow axial passage of a surgical implant, a surgical instrument, or a bodily passage such as a bone tunnel, a twenty-five to fifty percent reduction in suture traffic, or in the maximum number of suture thicknesses that simultaneously pass through the narrow passage, is achieved. Other embodiments are disclosed.

22 Claims, 6 Drawing Sheets

Related U.S. Application Data on Nov. 22, 2016, provisional application No. 62/456,217, filed on Feb. 8, 2017, provisional application No. 62/458,975, filed on Feb. 14, 2017.

(51) Int. Cl.

| | |
|---|---|
| *A61B 17/16* | (2006.01) |
| *A61B 90/00* | (2016.01) |
| *A61B 17/88* | (2006.01) |
| *A61B 17/80* | (2006.01) |
| *A61B 17/00* | (2006.01) |
| *A61B 17/84* | (2006.01) |

(52) U.S. Cl.
CPC ........ *A61B 17/1604* (2013.01); *A61B 17/885* (2013.01); *A61B 17/8869* (2013.01); *A61B 90/06* (2016.02); *A61B 17/80* (2013.01); *A61B 17/848* (2013.01); *A61B 2017/00526* (2013.01); *A61B 2017/00867* (2013.01); *A61B 2017/0403* (2013.01); *A61B 2017/0404* (2013.01); *A61B 2017/044* (2013.01); *A61B 2017/045* (2013.01); *A61B 2017/0409* (2013.01); *A61B 2017/0414* (2013.01); *A61B 2017/0441* (2013.01); *A61B 2017/0445* (2013.01); *A61B 2017/0453* (2013.01); *A61B 2017/0464* (2013.01); *A61B 2090/061* (2016.02)

(56) References Cited

U.S. PATENT DOCUMENTS

| | | |
|---|---|---|
| 2,362,957 A | 11/1944 | Hackett |
| 2,427,128 A | 9/1947 | Ettinger |
| 2,485,531 A | 10/1949 | William |
| 2,489,870 A | 11/1949 | William |
| 2,511,051 A | 6/1950 | William |
| 2,706,475 A | 4/1955 | Reynolds |
| 2,715,403 A | 8/1955 | Jordan |
| 3,114,367 A | 12/1963 | Carpenter |
| 3,664,022 A | 5/1972 | Small |
| 3,727,611 A | 4/1973 | Schultz |
| 3,867,932 A | 2/1975 | Huene |
| 3,959,960 A | 6/1976 | Santos |
| 4,050,464 A | 9/1977 | Hall |
| 4,159,716 A | 7/1979 | Borchers |
| 4,364,381 A | 12/1982 | Sher |
| D273,326 S | 4/1984 | Peterson |
| 4,586,497 A | 5/1986 | Dapra |
| 4,587,963 A | 5/1986 | Leibinger |
| 4,712,542 A | 12/1987 | Daniel |
| 4,787,377 A | 11/1988 | Laboureau |
| 4,945,904 A | 8/1990 | Bolton |
| 4,964,862 A | 10/1990 | Arms |
| 4,969,471 A | 11/1990 | Daniel |
| 4,969,895 A | 11/1990 | McLeod |
| 5,035,701 A | 7/1991 | Kabbara |
| 5,116,340 A | 5/1992 | Songer |
| 5,300,077 A | 4/1994 | Howell |
| 5,306,290 A | 4/1994 | Martins |
| 5,312,410 A | 5/1994 | Miller |
| 5,312,412 A | 5/1994 | Whipple |
| 5,409,490 A | 4/1995 | Ethridge |
| 5,431,659 A | 7/1995 | Ross, Jr. |
| 5,449,361 A | 9/1995 | Preissman |
| 5,476,465 A | 12/1995 | Preissman |
| 5,540,698 A | 7/1996 | Preissman |
| 5,545,168 A | 8/1996 | Burke |
| 5,570,706 A | 11/1996 | Howell |
| 5,578,057 A | 11/1996 | Wenstrom, Jr. |
| 5,584,839 A | 12/1996 | Gieringer |
| 5,643,321 A | 1/1997 | McDevitt |
| 5,713,897 A | 2/1998 | Goble |
| 5,725,532 A | 3/1998 | Shoemaker |
| 5,741,281 A | 4/1998 | Martin |
| 5,868,748 A | 2/1999 | Burke |
| 5,895,389 A | 4/1999 | Schenk |
| 6,001,106 A | 12/1999 | Ryan |
| 6,027,523 A | 2/2000 | Schmieding |
| 6,045,573 A | 4/2000 | Wenstrom |
| 6,254,604 B1 | 7/2001 | Howell |
| 6,254,605 B1 | 7/2001 | Howell |
| 6,368,326 B1 | 4/2002 | Dakin |
| 6,443,955 B1 | 9/2002 | Ahrend |
| 6,478,753 B2 | 11/2002 | Reay |
| 6,482,208 B1 | 11/2002 | Ahrend |
| 6,517,564 B1 | 2/2003 | Grafton |
| 6,527,794 B1 | 3/2003 | McDevitt |
| 6,547,778 B1 | 4/2003 | Sklar |
| 6,554,852 B1 | 4/2003 | Oberlander |
| 6,557,426 B2 | 5/2003 | Reinemann, Jr. |
| 6,616,667 B1 | 9/2003 | Steiger |
| 6,660,023 B2 | 12/2003 | McDevitt |
| 6,669,698 B1 | 12/2003 | Tromanhauser |
| 6,739,068 B1 | 5/2004 | Rinner |
| 6,761,722 B2 | 7/2004 | Cole |
| 6,780,198 B1 | 8/2004 | Gregoire |
| 6,866,673 B2 | 3/2005 | Oren |
| 7,060,068 B2 | 6/2006 | Tromanhauser |
| 7,081,126 B2 | 7/2006 | McDevitt |
| 7,083,638 B2 | 8/2006 | Foerster |
| 7,090,690 B2 | 8/2006 | Foerster |
| 7,160,285 B2 | 1/2007 | Sklar |
| 7,172,626 B1 | 2/2007 | Andrews |
| 7,211,088 B2 | 5/2007 | Grafton |
| 7,226,469 B2 | 6/2007 | Benavitz |
| 7,235,091 B2 | 6/2007 | Thornes |
| 7,326,222 B2 | 2/2008 | Dreyfuss |
| 7,431,692 B2 | 10/2008 | Zollinger |
| 7,442,202 B2 | 10/2008 | Dreyfuss |
| 7,455,683 B2 | 11/2008 | Geissler |
| 7,537,596 B2 | 5/2009 | Jensen |
| 7,556,630 B2 | 7/2009 | Molz |
| 7,572,275 B2 | 8/2009 | Fallin |
| 7,578,824 B2 | 8/2009 | Justin |
| 7,637,926 B2 | 12/2009 | Foerster |
| 7,871,368 B2 | 1/2011 | Zollinger |
| 7,875,058 B2 | 1/2011 | Holmes, Jr. |
| 7,887,551 B2 | 2/2011 | Bojarski |
| 7,901,431 B2 | 3/2011 | Shurnas |
| 7,963,966 B2 | 6/2011 | Cole |
| 7,998,149 B2 | 8/2011 | Hamilton |
| 8,083,769 B2 | 12/2011 | Cauldwell |
| 8,109,936 B2 | 2/2012 | Tipirneni |
| 8,114,127 B2 | 2/2012 | West |
| 8,114,128 B2 | 2/2012 | Cauldwell |
| 8,162,997 B2 | 4/2012 | Struhl |
| 8,167,906 B2 | 5/2012 | Cauldwell |
| 8,182,495 B2 | 5/2012 | DiStefano |
| 8,221,455 B2 | 7/2012 | Shurnas |
| 8,277,459 B2 | 10/2012 | Sand |
| 8,277,484 B2 | 10/2012 | Barbieri |
| 8,298,247 B2 | 10/2012 | Sterrett |
| 8,303,591 B1 | 11/2012 | Foerster |
| 8,317,828 B2 | 11/2012 | Martinek |
| 8,343,186 B2 | 1/2013 | Dreyfuss |
| 8,394,123 B2 | 3/2013 | Cauldwell |
| 8,414,599 B1 | 4/2013 | Foerster |
| 8,460,379 B2 | 6/2013 | Albertorio |
| 8,500,745 B2 | 8/2013 | Kuenzi |
| 8,506,597 B2 | 8/2013 | Kaiser |
| 8,579,901 B1 | 11/2013 | Foerster |
| 8,597,328 B2 | 12/2013 | Cauldwell |
| 8,613,755 B1 | 12/2013 | Foerster |
| 8,617,185 B2 | 12/2013 | Bonutti |
| 8,623,049 B2 | 1/2014 | Ward |
| 8,623,051 B2 | 1/2014 | Bojarski |
| 8,623,052 B2 | 1/2014 | Dreyfuss |
| 8,679,122 B2 | 3/2014 | Bernstein |
| 8,696,719 B2 | 4/2014 | Lofthouse |
| 8,715,297 B1 | 5/2014 | Foerster |
| 8,764,763 B2 | 7/2014 | Foerster |
| 8,764,797 B2 | 7/2014 | Dreyfuss |

(56) References Cited

U.S. PATENT DOCUMENTS

| | | |
|---|---|---|
| 8,790,344 B1 | 7/2014 | Foerster |
| 8,795,286 B2 | 8/2014 | Sand |
| 8,801,755 B2 | 8/2014 | Dreyfuss |
| 8,814,902 B2 | 8/2014 | Bonutti |
| 8,821,541 B2 | 9/2014 | Dreyfuss |
| 8,870,876 B2 | 10/2014 | Lettmann |
| 8,876,900 B2 | 11/2014 | Guederian |
| 8,882,833 B2 | 11/2014 | Saylor |
| 8,888,815 B2 | 11/2014 | Holmes, Jr. |
| 8,926,626 B2 | 1/2015 | Mannava |
| 8,939,999 B2 | 1/2015 | Sterrett |
| 8,945,026 B2 | 2/2015 | Moser |
| 8,961,575 B2 | 2/2015 | Choinski |
| 8,979,850 B2 | 3/2015 | Johnstone |
| 8,984,720 B2 | 3/2015 | Gephart |
| 9,017,330 B2 | 4/2015 | Foerster |
| 9,039,682 B2* | 5/2015 | Lampropoulos ...... A61M 25/02 606/1 |
| 9,072,509 B2 | 7/2015 | Stoll, Jr. |
| 9,107,701 B2 | 8/2015 | Cole |
| 9,131,937 B2 | 9/2015 | Chan |
| 9,138,219 B2 | 9/2015 | Horrell |
| 9,161,748 B2 | 10/2015 | West |
| 9,179,907 B2 | 11/2015 | ElAttrache |
| 9,179,950 B2 | 11/2015 | Zajac |
| 9,186,133 B2 | 11/2015 | Gregoire |
| 9,204,872 B2 | 12/2015 | Loepke |
| 9,259,217 B2 | 2/2016 | Fritzinger |
| 9,271,715 B2 | 3/2016 | Cauldwell |
| 9,277,912 B2 | 3/2016 | Donate |
| 9,521,999 B2 | 12/2016 | Dreyfuss |
| 9,526,493 B2 | 12/2016 | Dreyfuss |
| 9,532,776 B2 | 1/2017 | Lo |
| 9,549,726 B2 | 1/2017 | Dreyfuss |
| 9,622,739 B2 | 4/2017 | Dreyfuss |
| 2001/0049483 A1 | 12/2001 | Reay |
| 2002/0087190 A1 | 7/2002 | Benavitz |
| 2002/0188297 A1 | 12/2002 | Dakin |
| 2003/0009171 A1 | 1/2003 | Tornier |
| 2003/0176920 A1 | 9/2003 | Sklar |
| 2004/0098045 A1 | 5/2004 | Grafton |
| 2004/0102788 A1 | 5/2004 | Huebner |
| 2004/0153153 A1 | 8/2004 | Elson |
| 2005/0065533 A1 | 3/2005 | Magen |
| 2005/0070906 A1 | 3/2005 | Clark |
| 2005/0222618 A1 | 10/2005 | Dreyfuss |
| 2005/0240226 A1 | 10/2005 | Foerster |
| 2006/0085006 A1 | 4/2006 | Ek |
| 2006/0161159 A1 | 7/2006 | Dreyfuss |
| 2006/0271060 A1 | 11/2006 | Gordon |
| 2006/0276804 A1 | 12/2006 | Molz |
| 2006/0293709 A1 | 12/2006 | Bojarski |
| 2007/0060922 A1 | 3/2007 | Dreyfuss |
| 2007/0060931 A1 | 3/2007 | Hamilton |
| 2007/0073299 A1 | 3/2007 | Dreyfuss |
| 2007/0083236 A1 | 4/2007 | Sikora |
| 2007/0088362 A1 | 4/2007 | Bonutti |
| 2007/0150003 A1 | 6/2007 | Dreyfuss |
| 2007/0198036 A1 | 8/2007 | Sklar |
| 2007/0225764 A1 | 9/2007 | Benavitz |
| 2007/0288027 A1 | 12/2007 | Grafton |
| 2008/0077182 A1 | 3/2008 | Geissler |
| 2009/0043153 A1 | 2/2009 | Zollinger |
| 2009/0228049 A1 | 9/2009 | Park |
| 2009/0306711 A1 | 12/2009 | Stone et al. |
| 2010/0010496 A1 | 1/2010 | Isaza |
| 2010/0160963 A1 | 6/2010 | Fallin |
| 2010/0191284 A1 | 7/2010 | Dreyfuss |
| 2010/0262185 A1 | 10/2010 | Gelfand |
| 2011/0022054 A1 | 1/2011 | DiStefano |
| 2011/0112576 A1 | 5/2011 | Nguyen |
| 2011/0184426 A1 | 7/2011 | Garces Martin |
| 2011/0224727 A1 | 9/2011 | Housman |
| 2012/0053626 A1 | 3/2012 | Koepke |
| 2012/0065677 A1 | 3/2012 | West |
| 2012/0123417 A1 | 5/2012 | Smith |
| 2012/0123428 A1 | 5/2012 | Berberich |
| 2012/0165867 A1 | 6/2012 | Denham et al. |
| 2012/0172936 A1 | 7/2012 | Horrell |
| 2012/0253410 A1 | 10/2012 | Taylor |
| 2013/0023930 A1 | 1/2013 | Stone et al. |
| 2013/0138150 A1 | 5/2013 | Baker |
| 2013/0165972 A1 | 6/2013 | Sullivan |
| 2013/0184708 A1 | 7/2013 | Robinson |
| 2013/0296937 A1 | 11/2013 | Dreyfuss |
| 2013/0345750 A1 | 12/2013 | Sullivan |
| 2014/0018828 A1 | 1/2014 | Foerster |
| 2014/0031882 A1 | 1/2014 | Schmuck |
| 2014/0039551 A1 | 2/2014 | Donahue |
| 2014/0074163 A1 | 3/2014 | West |
| 2014/0081322 A1 | 3/2014 | Sengun |
| 2014/0081323 A1 | 3/2014 | Hawkins |
| 2014/0081324 A1 | 3/2014 | Sengun |
| 2014/0081325 A1 | 3/2014 | Sengun |
| 2014/0114353 A1 | 4/2014 | Bojarski |
| 2014/0121701 A1 | 5/2014 | Dreyfuss |
| 2014/0128915 A1 | 5/2014 | Dreyfuss |
| 2014/0194907 A1 | 7/2014 | Bonutti |
| 2014/0194927 A1 | 7/2014 | Kaiser |
| 2014/0277154 A1 | 9/2014 | ElAttrache |
| 2014/0364905 A1 | 12/2014 | Lunn |
| 2014/0364909 A1 | 12/2014 | Dreyfuss |
| 2014/0371749 A1 | 12/2014 | Foerster |
| 2014/0379028 A1 | 12/2014 | Lo |
| 2015/0005779 A1 | 1/2015 | Tepic |
| 2015/0005819 A1 | 1/2015 | Dreyfuss |
| 2015/0012015 A1 | 1/2015 | Berelsman |
| 2015/0039029 A1 | 2/2015 | Wade |
| 2015/0051601 A1 | 2/2015 | Larsen |
| 2015/0073475 A1 | 3/2015 | Schaller |
| 2015/0073477 A1 | 3/2015 | Holmes, Jr. |
| 2015/0173739 A1 | 6/2015 | Rodriguez et al. |
| 2015/0201923 A1 | 7/2015 | Fan |
| 2015/0216576 A1 | 8/2015 | Foerster |
| 2015/0272567 A1 | 10/2015 | Feezor |
| 2015/0289868 A1* | 10/2015 | Sauer ................ A61B 17/0401 606/144 |
| 2015/0305737 A1 | 10/2015 | Conley |
| 2015/0313640 A1 | 11/2015 | O'Daly |
| 2015/0342594 A1 | 12/2015 | Stone |
| 2015/0342596 A1 | 12/2015 | Dreyfuss |
| 2015/0342651 A1 | 12/2015 | Cole |
| 2015/0351741 A1 | 12/2015 | Hawkins |
| 2016/0008041 A1 | 1/2016 | Makhlouf |
| 2016/0038201 A1 | 2/2016 | Cummings |
| 2016/0038267 A1 | 2/2016 | Allen |
| 2016/0051250 A1 | 2/2016 | Thornes |
| 2016/0051251 A1 | 2/2016 | Koepke |
| 2016/0066901 A1 | 3/2016 | Gregoire |
| 2016/0089131 A1 | 3/2016 | Wade |
| 2016/0192924 A1 | 7/2016 | Cauldwell |
| 2016/0235399 A1 | 8/2016 | Housman |
| 2016/0270902 A1 | 9/2016 | Snedeker et al. |
| 2016/0287302 A1 | 10/2016 | Horrell |
| 2016/0374661 A1 | 12/2016 | Housman et al. |
| 2017/0071592 A1 | 3/2017 | Feezor et al. |

FOREIGN PATENT DOCUMENTS

| | | |
|---|---|---|
| ES | 2226791 T3 | 4/2005 |
| JP | 2002102236 A | 4/2002 |
| WO | 2011153417 A1 | 12/2011 |
| WO | 2012092027 A2 | 7/2012 |

OTHER PUBLICATIONS

International Search Report and Written Opinion for Int. Appl. No. PCT/US2017/064178 dated Mar. 9, 2018, 9 pp.
Akros Fibulink, Akros Medical, 2017, www.akrosmedical.com, 3 pp.
Deltoid Ligament Reconstruction Tunnel Sites, Arthrex, Inc., www.arthrex.com, 2014, 2 pp.

(56) References Cited

OTHER PUBLICATIONS

InternalBrace—Ligament Augmentaion Repair—Deltoid Ligament, Arthex, Inc., www.arthrex.com, 2015, 2 pp.
InternalBrace—Advanced Treatment for Ligament & Tendon Repair, Arthrex, Inc., www.arthrex.com, 2 pp.
InternalBrace—Ligament Augmentation Repair, Arthrex, Inc., www.arthrex.com, 2015, 2 pp.
Modified Brostrom-Gould Technique for Lateral Ankle Ligament Reconstruction—Surgical Technique, Arthrex, Inc., www.arthrex.com, 2015, 6 pp.
Knotless TightRope Syndesmosis Fixation—Surgical Technique, Arthrex, Inc., www.arthrex.com, 2015, 5 pp.
Get your athlete back in the game!—Syndesmosis TightRope, Arthrex, Inc., http://cptr.it/TRHAS, 2015, 1 pp.
ZipTight Fixation System, BioMet Sports Medicine, www.biometsportsmedicine.com, 2009, 8 pp.
Nelson, Owen A., "Examination and Repair of the AITFL in Transmalleolar Fractures", J. Orthop Trauma, vol. 20, No. 9, Oct. 2006, p. 637-643.
Invisiknot—Foot and Ankle Technique Guide—Ankle Syndesmosis Repair, Operative Technique, Smith & Nephew, Inc., www.smith-nephew.com, Jun. 2017, 8 pp.
Invisiknot—Ankle Syndesmosis Repair Kit, Smith & Nephew, Inc., www.smith-nephew.com, 1 pp.
Van Fieest, Tyler J., et al., "Injureis to the Ankle Syndesmosis", J. Bone Joint Surg. Am. 2014;96:603-13, http://dx.dor.org/10.2106/JBJS.M.00094, 11 pp.

* cited by examiner

MULTIPLE SUTURE THREADER AND METHODS OF USE

REFERENCE TO PENDING PRIOR PATENT APPLICATIONS

This application claims the benefit under 35 U.S.C. 119(e) of U.S. Provisional Patent Application Nos. 62/358,231, filed Jul. 5, 2016 by Justin Taber and T. Wade Fallin for "LIGAMENT REINFORCEMENT DEVICES AND METHODS," 62/425,560 filed Nov. 22, 2016 by Justin Tabor, Phinit Phisitkul, and T. Wade Fallin for "LIGAMENT REINFORCEMENT DEVICES AND METHODS," 62/456,217, filed Feb. 8, 2017 by Justin Taber and T. Wade Fallin for "PLATE AND LOOP CONSTRUCT," and 62/458,975, filed Feb. 14, 2017 by Matthew Karam, Phinit Phisitkul, Justin Taber, and T. Wade Fallin for "PELVIC FRACTURE REPAIR," all of which patent applications are hereby incorporated herein by reference.

REFERENCE TO CO-FILED APPLICATIONS

This application was co-filed with the following U.S. Patent Application Numbers on Jul. 5, 2017: Ser. No. 15/641,573, by Matthew Karam, Phinit Phisitkul, Justin Taber, and T. Wade Fallin for "INTRA JOINT STABILIZATION CONSTRUCT,"; Ser. No. 15/641,592, by Justin Taber and T. Wade Fallin for "EXTRA JOINT STABILIZATION CONSTRUCT,"; Ser. No. 15/641,600 by Justin Taber and T. Wade Fallin for "NONCIRCULAR BROACH AND METHODS OF USE,"; and Ser. No. 15/642,053 by Justin Taber and T. Wade Fallin for "COMPRESSION AND TENSION INSTRUMENTS AND METHODS OF USE TO REINFORCE LIGAMENTS,"; all of which patent applications are incorporated herein by reference.

BACKGROUND

Suture threaders or suture passers are devices used to pass a suture through material passages such as, for example, bodily tissue passages/lumen of a surgical patient, surgical implants such as fixation or anchor hardware, or cannulas formed within surgical instruments. Oftentimes sutures must be passed or threaded through a narrow passage through a patient's bone tunnel or arterial or intestinal lumen, or through a cannula or sleeve incorporated within a surgical instrument or another piece of surgical hardware. When a loop-style suture threader is employed, the sutures are doubled over the loop, which creates excess bulk that cannot easily be passed through the narrow passage.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a suture threader for passing at least first and second sutures, each having first and second opposing ends, through a passage having a proximal opening and a distal opening in a manner that reduces suture traffic through the passage. The suture threader includes (1) a handle; (2) a first collapsible loop suspended from the handle at a first distal offset, the first collapsible loop configured to receive the first end of the first suture doubled over the first collapsible loop; and (3) a second collapsible loop suspended from the handle at a second distal offset from the first collapsible loop. The second collapsible loop is configured to receive the first end of the second suture doubled over the second collapsible loop, wherein when the first and the second collapsible loops are passed through the passage to draw the first and the second sutures through the passage such that the first ends of the first and the second sutures are located proximal to the proximal opening of the passage and the second ends of the first and the second sutures are located distal to the distal opening of the passage, a total number of suture thicknesses to pass simultaneously through the passage is limited to three.

Another embodiment provides a method of threading multiple sutures through an axial passage. The method includes the steps of (1) providing a suture threader having a proximal end and a distal end, a first collapsible loop located at a first distal offset from the proximal end, and a second collapsible loop located at a second distal offset from the first collapsible loop; (2) passing the first and the second collapsible loops of the suture threader through the axial passage such that the axial passage is positioned along the first distal offset; (3) threading one or more first threads through the first collapsible loop such that a first end of each of the one or more of the first threads is doubled over the first collapsible loop; (4) threading one or more second threads through the second collapsible loop such that a first end of each of the one or more of the second threads is doubled over the second collapsible loop; (5) pulling the first collapsible loop through the axial passage until each of the first ends of the one or more of the first sutures exits a proximal end of the axial passage; and (6) pulling the second collapsible loop through the axial passage until each of the first ends of the one or more of the second sutures exits the proximal end of the axial passage, wherein a maximum number of suture thicknesses to simultaneously pass through the axial passage equals one thickness for each of the one or more of the first threads plus two thicknesses for each of the one or more of the second threads.

Yet another embodiment provides a method of reducing suture traffic through an axial passage using a suture threader having a handle located at a proximal end of the suture threader, a first collapsible loop located at a first distal offset from the handle, and a second collapsible loop located at a second distal offset from the first collapsible loop. The method includes the steps of (1) passing the first and the second collapsible loops of the suture threader through the axial passage such that the handle is located proximal to the axial passage and the first and the second collapsible loops are located distal to the axial passage; (2) providing at least a first suture and a second suture, each of the first and the second sutures having first and second opposing ends; (3) doubling the first end of the first suture over the first collapsible loop to form first and second thicknesses at the first end of the first suture; (4) doubling the first end of the second suture over the second collapsible loop to form first and second thicknesses at the first end of the second suture; (5) first pulling the first collapsible loop through the axial passage such that when the first end of the first suture passes through the axial passage, the first and the second thicknesses of the first suture are located within the axial passage, and when the first end of the first suture exits the axial passage, the second thickness of the first suture remains within the axial passage; and (6) second pulling the second collapsible loop through the axial passage such that when the first end of the second suture passes through the axial passage, the second thickness of the first suture and the first and the second thicknesses of the second suture are located within the axial passage, and when the first end of the second suture exits the axial passage, the second thickness of the first suture and the second thickness of the second suture remain within the axial passage.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

The technology discussed herein relates to apparatus and corresponding methods of use for threading sutures through narrow passages in a manner that reduces the amount of material passed at any one time through a passage such as, for example, an instrument cannula, a surgical implant sheath or tube, a bodily lumen (e.g., an arterial lumen, an intestinal lumen), a bone tunnel, and so on. This reduction in the amount of pass-through material allows for a reduced passage diameter and, in instances of a passage through an item of medical hardware, a reduced size of the associated device or hardware forming the passage (e.g., reduced size of suture fixation hardware, reduced size of a bone tunnel sheath, etc.).

Figure 1A:
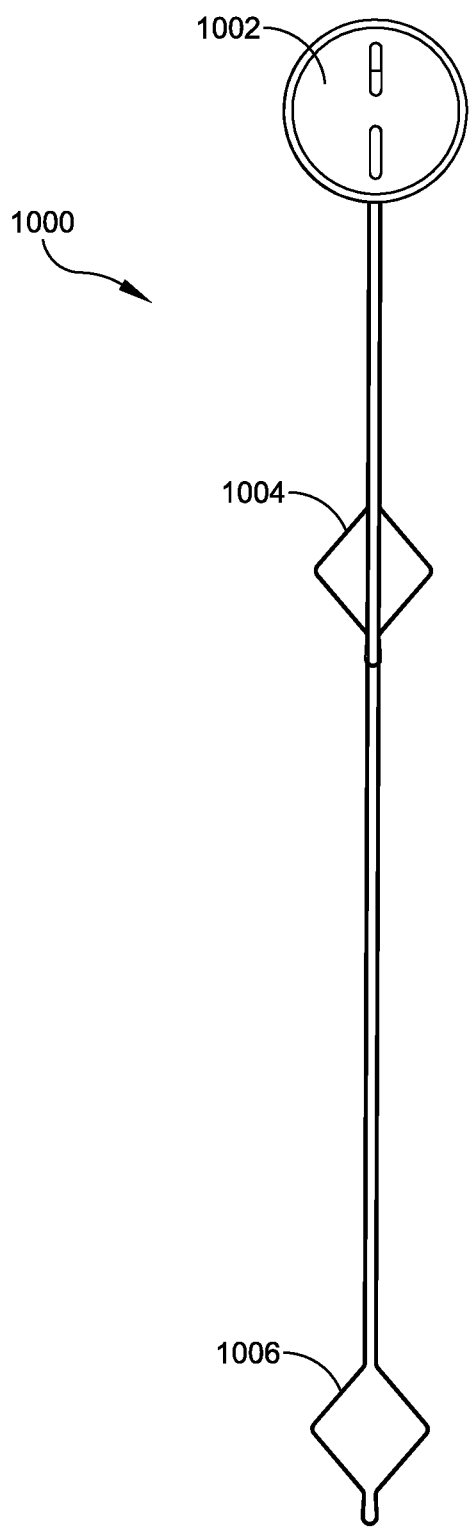
FIGS. 1A-1B illustrate respective front and perspective views of one embodiment of a multiple suture threader.
Figure 1B:
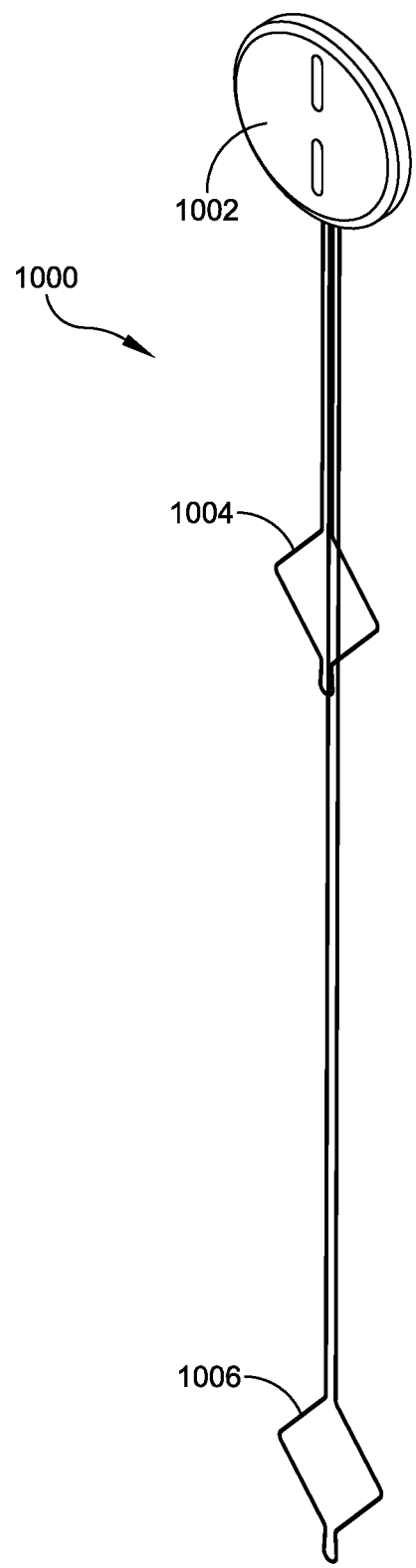

FIGS. 1A-1B illustrate front and perspective views of one embodiment of a suture threader 1000 for use with any passage through which the threading of suture or another flexible strand is desired in an implant, instrument, tissue, or otherwise. In this embodiment, suture threader 1000 may include a handle 1002, a first collapsible loop 1004 connected to the handle 1002, and a second collapsible loop 1006 independently connected to the handle 1002. The second loop 1006 is spaced or offset distally relative to the first loop 1004. In this embodiment, the two loops 1004, 1006 may be formed of and suspended from the handle by discrete strands or filaments of any appropriate material such as, for example, a flexible wire. In another embodiment, one or both of loop 1002 or loop 1004 may be provided in a non-collapsible configuration, which may include, but is not limited to, a rigid configuration, a flexible configuration, or a semi-flexible configuration. Preferably they are formed from a shape memory material such as nitinol wire. Both of the loops 1004, 1006 are configured to pass through the passage through which suture is to be passed.

Figure 2:
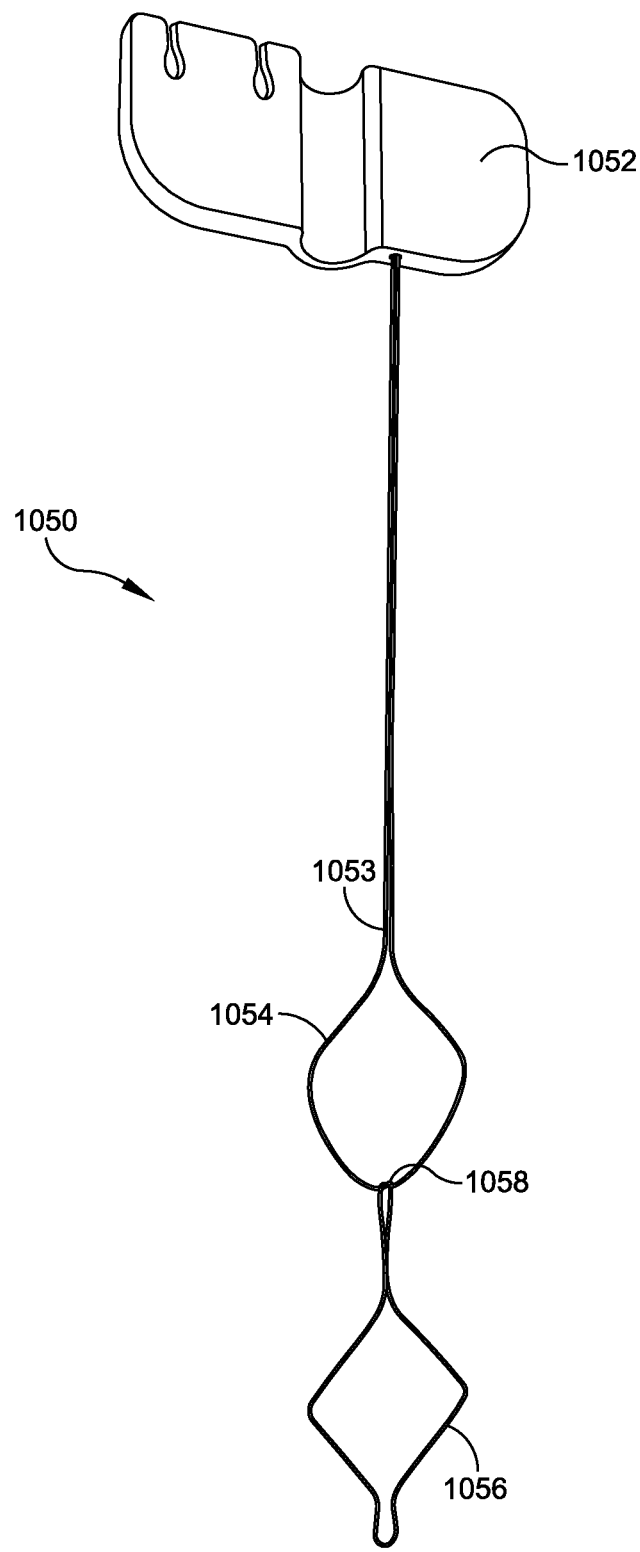
FIG. 2 illustrates a perspective view another embodiment of a multiple suture threader.

FIG. 2 illustrates an alternative embodiment of a multiple suture threader 1050, which is similar to threader 1000. However, rather than two discreet collapsible loops 1004, 1006 formed of separate strands or wires that are each discretely connected with the handle 1002, threader 1050 includes a single filament 1053 that connects with the handle 1050 and forms both a first proximal collapsible loop 1054 and a second distal collapsible loop 1056. A base 1058 of the first collapsible loop 1054 may be formed by crossing the filament 1053 over itself at the base 1058 before forming the second distal collapsible loop 1056. In other embodiments, the base 1058 of the first collapsible loop 1054 may be formed via other methods such as, for example, laser welding, adhesive bonding, diffusion bonding, and/or crimping.

In some embodiments, the first and the second collapsible loops 1054, 1056 may be formed of a polymer strand such as a monofilament or a braided suture. In these embodiments, the base 1058 of the first collapsible loop 1054 may be formed via any appropriate method including, for example, adhesive bonding, ultrasonic welding, radio frequency welding, or melt bonding.

Figure 3:
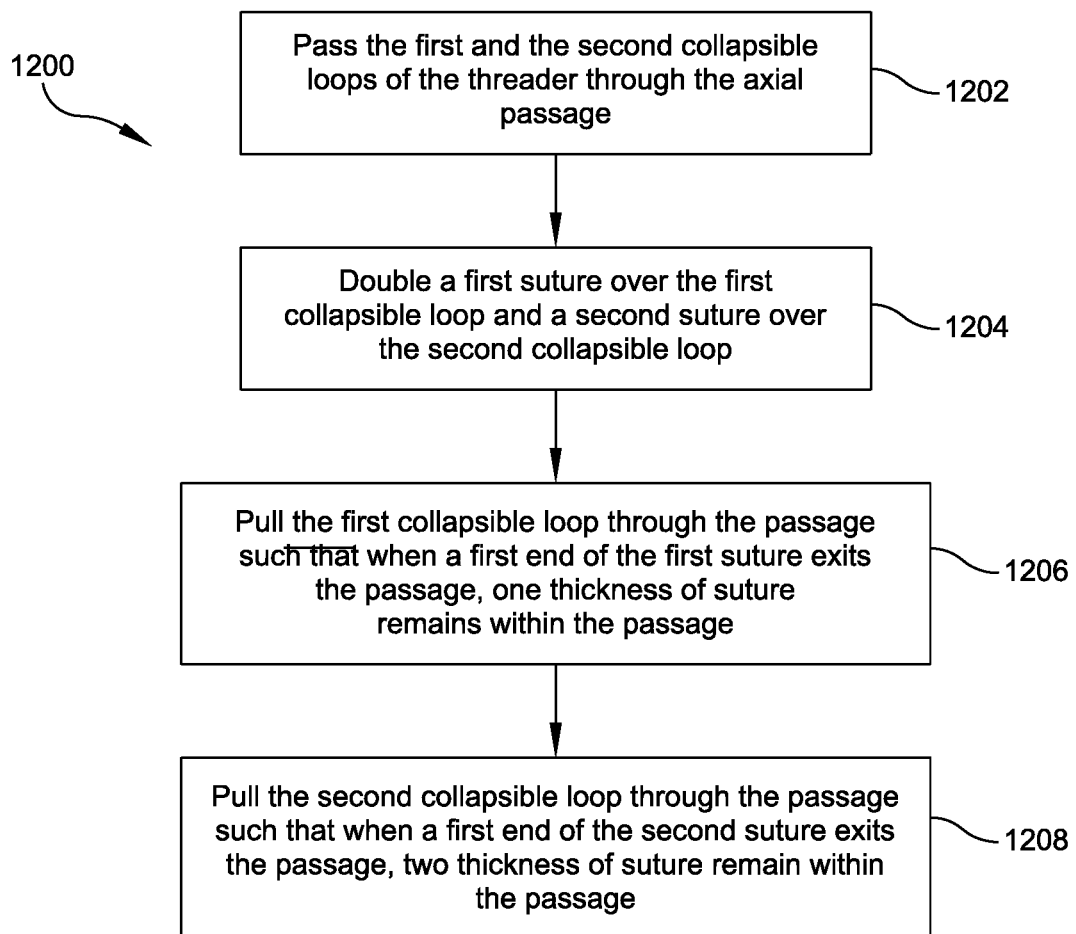
FIG. 3 provides a flowchart depicting an exemplary process for threading sutures through a narrow passage using the multiple suture threader of FIGS. 1A-1B.

FIG. 3 provides a flowchart detailing an exemplary threading process 1200 using the exemplary threader 1000, while FIGS. 4-7 illustrate the corresponding steps of the threading process 1200. FIGS. 4-7 show the suture threader 1000 in use with a generic sleeve 1008, though it should be understood that embodiments of the threaders 1000, 1050 may be used to thread a suture 1010 or other flexible strand though any passage through which suture threading is desired in an implant, an instrument, human tissue, or otherwise. For example, embodiments of the suture threaders 1000, 1050 may be used with the fixation anchor 1440 disclosed in FIGS. 26-29 of U.S. patent application Ser. No. 15/641,573, entitled "INTRA JOINT STABILIZATION CONSTRUCT"; and co-filed with this application on Jul. 5, 2017 or with any other appropriate fixation hardware, implant, instrument, or human tissue lumen.

Figure 4:
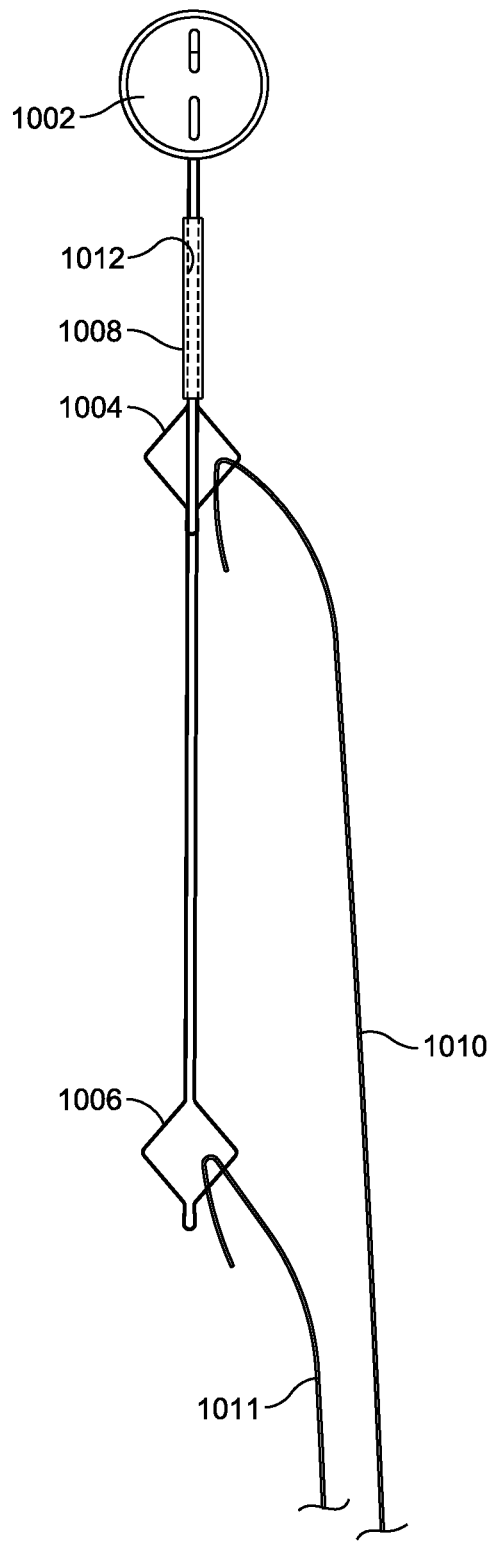
FIG. 4 illustrates a front view of the multiple suture threader of FIGS. 1A-1B with a first collapsible loop and a second collapsible loop in a starting position relative to the narrow passage.

The exemplary threading process 1200 begins, as shown in FIG. 4, with the loops 1004, 1006 being passed through an axial passage 1012 of the sleeve 1008 (FIG. 3, 1202). One or more first sutures 1010 are then doubled over the first loop 1004, and one or more second sutures 1011 are doubled over the second loop 1006 (FIG. 3, 1204). In the example of FIGS. 4-7, a single suture is doubled over each loop 1004, 1006. However, the threader 1000 may be used with one or more sutures 1010, 1011 doubled over each loop in any desired and/or appropriate combination.

Figure 5:
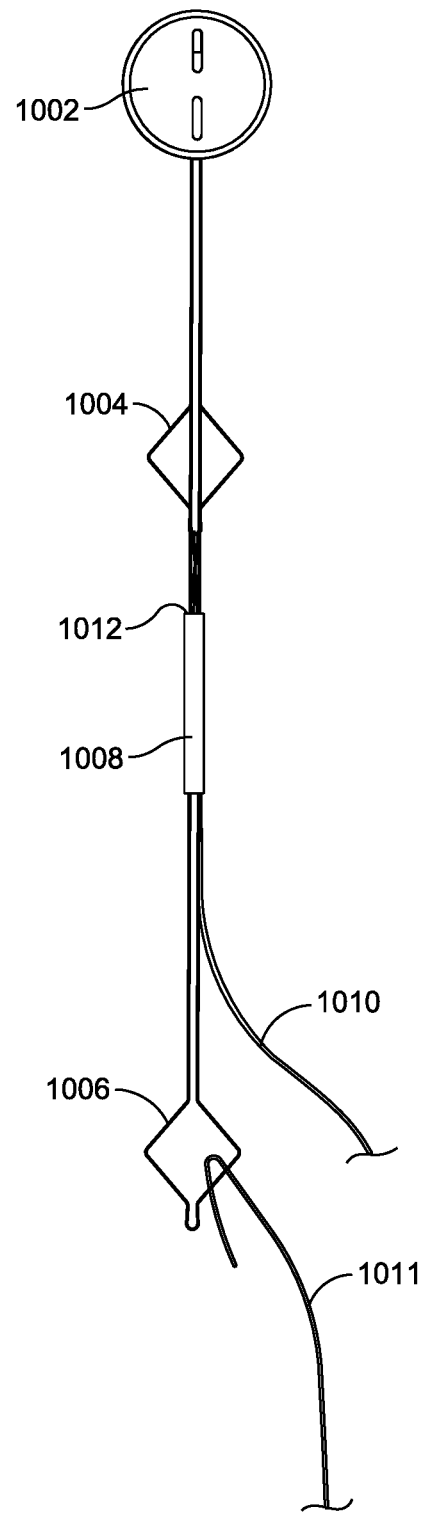
FIG. 5 illustrates a front view of the multiple suture threader after the first collapsible loop and a doubled first suture have been passed through the narrow passage.
Figure 6:
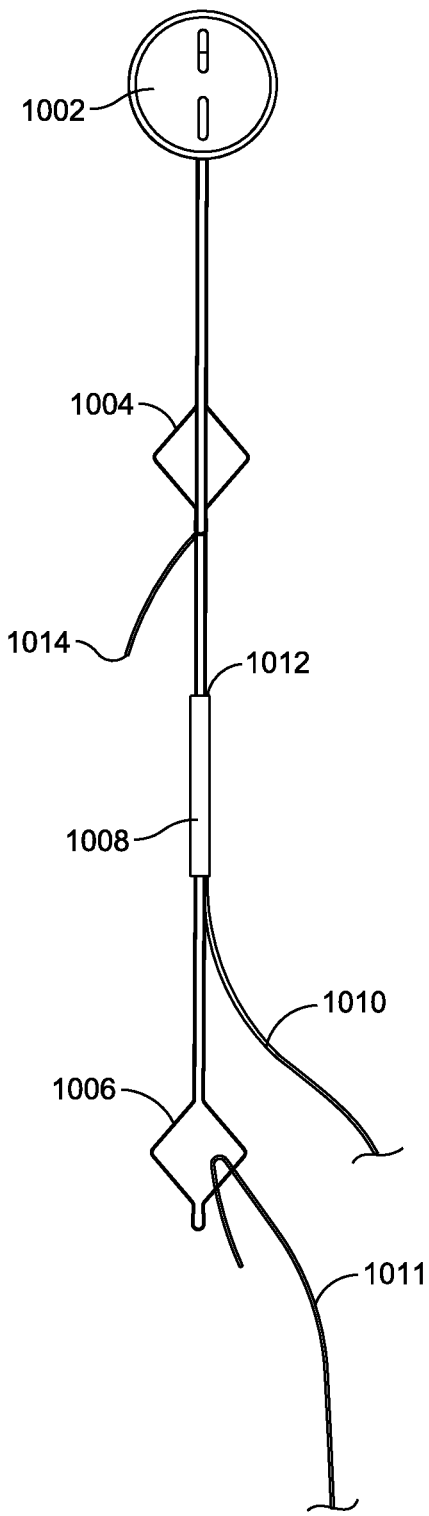
FIG. 6 illustrates a front view of the multiple suture threader after a first end of the first suture has exited the narrow passage.
Figure 7:
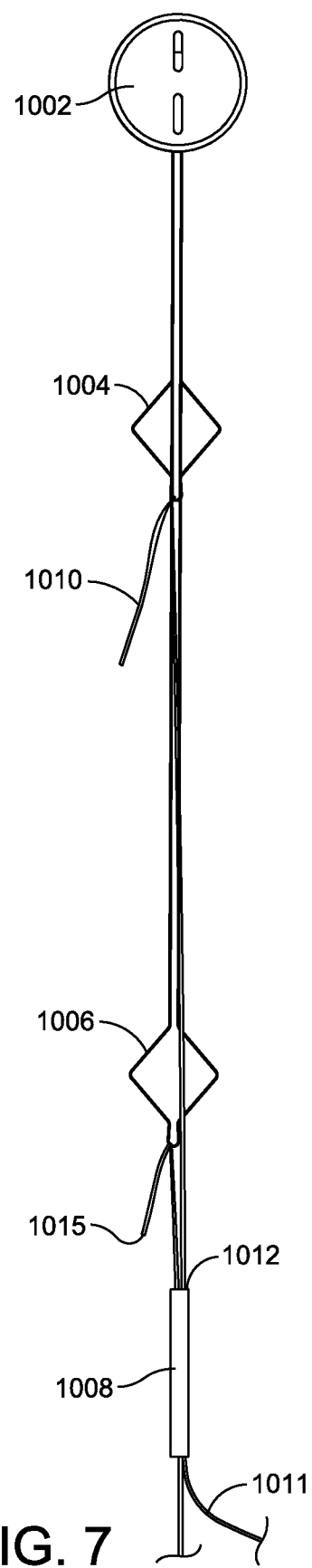
FIG. 7 illustrates a front view of the multiple suture threader after the second collapsible loop and a first end of the second suture have exited the narrow passage.

In FIG. 5, the first collapsible loop 1004 has been pulled through the passage 1012 formed within the sleeve 1008 (FIG. 3, 1206). At the position shown in FIG. 5, two thicknesses of the first suture 1010 are being passed through the passage 1012 due to the first suture 1010 being doubled over. At the position shown in FIG. 6, a first end 1014 of the first suture 1010 has exited the passage 1012 so that only one thickness of the first suture 1010 remains within the passage 1012.

Further pulling of the threader 1000 pulls the second collapsible loop 1006 into the passage 1012 (FIG. 3, 1208). At this point, three suture thicknesses remain within the passage—one thickness of the first suture 1010 and two thicknesses of the second suture 1011. At the position shown in FIG. 7, both the first and the second loops 1004, 1006 have exited the passage 1012, along with a first end 1015 of the second suture 1011. At this point, only two thicknesses of suture—one thickness each of the first suture 1010 and the second suture 1011—remain within the passage 1012.

By separating the first and the second collapsible loops 1004, 1006 axially, the maximum number of suture thicknesses that must be passed simultaneously to thread a given number of sutures through the passage 1012 is reduced. If the number of sutures doubled over each loop is the same, then the total suture thickness that must be passed is reduced by 25%. For example, as described above, if one suture is doubled over each of the first and the second collapsible loops 1004, 1006, then the maximum number of suture thicknesses that must be passed simultaneously to thread both of the sutures is three, a 25% reduction from the four suture thicknesses that must be passed simultaneously if two sutures are doubled over a traditional single loop threader. In another example, if two sutures are doubled over each of the first and the second loops 1004, 1006, then the maximum number of suture thicknesses that must be passed simultaneously to thread all four sutures is limited to six. With a traditional threader, the maximum number of suture thicknesses that must be passed simultaneously to thread all four sutures is eight, or the total number of sutures doubled over the single loop of the traditional threader (i.e., 4×2). In a further example, if three sutures are doubled over each of the first and the second loops 1004, 1006, then the maximum number of suture thicknesses that must be passed simultaneously to thread all six sutures is nine. With a traditional threader, the maximum number of suture thicknesses that must be passed simultaneously to thread all six sutures is twelve, or the total number of sutures doubled over the single loop of the traditional threader (i.e., 6×2).

Notably, any number of threads may be doubled over each of the first and the second loops 1004, 1006, and the numbers may be equal across the two loops or different, as appropriate. Depending on the use and the varying numbers of sutures doubled over each of the first and the loops, embodiments of the multiple suture threaders 1000, 1050 may achieve up to a 50% reduction in suture traffic.

Further, while the embodiments shown in FIGS. 1-2 and 4-7 features two axially-spaced collapsible loops, other embodiments may feature additional axially spaced loops, as desired for a variety of threading applications.

Embodiments of the threader disclosed herein are particularly advantageous where sutures need to be passed through a narrow passage. When sutures are threaded using a loop-style suture threader, the sutures are doubled over the loop. With a narrow passage and multiple sutures, the doubled over ends create excess bulk that cannot be easily passed through the passage. The suture threaders 1000, 1050 reduces the suture traffic through the passage, or reduce the number of suture thicknesses that must be passed simultaneously by spacing the doubled over ends axially apart so that only a portion of the doubled over ends is passed through the passage at any one time.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method of threading multiple sutures through an axial passage, comprising:
    positioning a suture threader proximate the axial passage, the suture threader having a proximal end and a distal end, a first collapsible loop located at a first distal offset from the proximal end, and a second collapsible loop located at a second distal offset from the first collapsible loop;
    passing the first and the second collapsible loops of the suture threader through the axial passage such that the axial passage is positioned along the first distal offset;
    with the axial passage positioned in a human body, threading one or more first threads through the first collapsible loop such that a first end of each of the one or more of the first threads is doubled over the first collapsible loop;
    threading one or more second threads through the second collapsible loop such that a first end of each of the one or more of the second threads is doubled over the second collapsible loop;
    pulling the first collapsible loop through the axial passage until each of the first ends of the one or more of the first threads exits a proximal end of the axial passage; and
    pulling the second collapsible loop through the axial passage until each of the first ends of the one or more of the second threads exits the proximal end of the axial passage, wherein a maximum number of suture thicknesses to simultaneously pass through the axial passage equals one thickness for each of the one or more of the first threads plus two thicknesses for each of the one or more of the second threads.

2. The method of claim 1, wherein the suture threader further includes a handle attached at the proximal end of the threader.

3. The method of claim 2, wherein the first flexible loop is suspended from the handle via a first filament and the second flexible loop is suspended from the handle via a second filament.

4. The method of claim 2, wherein the first and the second flexible loops are suspended from the handle via a common filament.

5. The method of claim 4, wherein a distal base of the first collapsible loop is formed via one of crossing the common filament over itself, laser welding, adhesive bonding, diffusion bonding, crimping, ultrasonic welding, radio frequency welding, and melt bonding.

6. The method of claim 1, wherein the first and the second collapsible loops are formed of flexible wire or polymer strand.

7. The method of claim 1, wherein:
    the passing the first and the second collapsible loops of the suture threader through the axial passage comprises pushing the first and the second collapsible loops of the suture threader through the axial passage in a proximal-to-distal direction;

the pulling the first collapsible loop through the axial passage until each of the first ends of the one or more of the first threads exits a proximal end of the axial passage comprises pulling the first collapsible loop through the axial passage in a distal-to-proximal direction; and the pulling the second collapsible loop through the axial passage until each of the first ends of the one or more of the second threads exits the proximal end of the axial passage comprises pulling the second collapsible loop through the axial passage in the distal-to-proximal direction.

8. A method of reducing suture traffic through an axial passage using a suture threader having a handle located at a proximal end of the suture threader, a first collapsible loop located at a first distal offset from the handle, and a second collapsible loop located at a second distal offset from the first collapsible loop, the method comprising:

with the suture threader positioned proximate a human body, passing the first and the second collapsible loops of the suture threader through the axial passage such that the handle is located proximal to the axial passage and the first and the second collapsible loops are located distal to the axial passage;

positioning at least a first suture and a second suture proximate the suture threader, each of the first and the second sutures having first and second opposing ends;

doubling the first end of the first suture over the first collapsible loop to form first and second thicknesses at the first end of the first suture;

doubling the first end of the second suture over the second collapsible loop to form first and second thicknesses at the first end of the second suture;

first pulling the first collapsible loop through the axial passage such that when the first end of the first suture passes through the axial passage, the first and the second thicknesses of the first suture are located within the axial passage, and when the first end of the first suture exits the axial passage, the second thickness of the first suture remains within the axial passage; and second pulling the second collapsible loop through the axial passage such that when the first end of the second suture passes through the axial passage, the second thickness of the first suture and the first and the second thicknesses of the second suture are located within the axial passage, and when the first end of the second suture exits the axial passage, the second thickness of the first suture and the second thickness of the second suture remain within the axial passage.

9. The method of claim 8, wherein the first and the second collapsible loops are formed from a common wire suspended from the handle.

10. The method of claim 9, wherein a distal base of the first collapsible loop is formed via one of crossing the common wire over itself, laser welding, adhesive bonding, diffusion bonding, and crimping.

11. The method of claim 8, wherein the first and the second collapsible loops are formed of flexible wire or polymer strand.

12. The method of claim 8, wherein the axial passage forms a pathway through a cannula of a surgical instrument, a sheath of a surgical implant, a bodily lumen, or a bone tunnel.

13. The method of claim 12, further comprising, prior to passing the first and the second collapsible loops of the suture threader through the axial passage, forming the axial passage in the human body such that the axial passage forms a pathway through a bodily lumen or a bone tunnel.

14. The method of claim 8, wherein:

the passing the first and the second collapsible loops of the suture threader through the axial passage comprises pushing the suture threader through the axial passage in a proximal-to-distal direction;

the first pulling the first collapsible loop through the axial passage comprises pulling the first collapsible loop through the axial passage in a distal-to-proximal direction; and the second pulling the second collapsible loop through the axial passage comprises pulling the first collapsible loop through the axial passage in the distal-to-proximal direction.

15. A method of threading multiple sutures through an axial passage, comprising:

positioning a suture threader proximate the axial passage, the suture threader having a proximal end and a distal end, a first collapsible loop located at a first distal offset from the proximal end, and a second collapsible loop located at a second distal offset from the first collapsible loop;

threading one or more first threads through the first collapsible loop such that a first end of each of the one or more of the first threads is doubled over the first collapsible loop;

threading one or more second threads through the second collapsible loop such that a first end of each of the one or more of the second threads is doubled over the second collapsible loop;

with the axial passage positioned in a human body, along the first distal offset, pulling the first collapsible loop through the axial passage until each of the first ends of the one or more of the first threads exits a proximal end of the axial passage; and pulling the second collapsible loop through the axial passage until each of the first ends of the one or more of the second threads exits the proximal end of the axial passage, wherein a maximum number of suture thicknesses to simultaneously pass through the axial passage equals one thickness for each of the one or more of the first threads plus two thicknesses for each of the one or more of the second threads.

16. The method of claim 15, wherein the suture threader further includes a handle attached at the proximal end of the threader.

17. The method of claim 16, wherein the first flexible loop is suspended from the handle via a first filament and the second flexible loop is suspended from the handle via a second filament.

18. The method of claim 16, wherein the first and the second flexible loops are suspended from the handle via a common filament.

19. The method of claim 18, wherein a distal base of the first collapsible loop is formed via one of crossing the common filament over itself, laser welding, adhesive bonding, diffusion bonding, crimping, ultrasonic welding, radio frequency welding, and melt bonding.

20. The method of claim 15, wherein the first and the second collapsible loops are formed of flexible wire or polymer strand.

21. The method of claim 15, wherein:
the passing the first and the second collapsible loops of the suture threader through the axial passage comprises pushing the first and the second collapsible loops of the suture threader through the axial passage in a proximal-to-distal direction;
the pulling the first collapsible loop through the axial passage until each of the first ends of the one or more of the first threads exits a proximal end of the axial passage comprises pulling the first collapsible loop through the axial passage in a distal-to-proximal direction; and
the pulling the second collapsible loop through the axial passage until each of the first ends of the one or more of the second threads exits the proximal end of the axial passage comprises pulling the second collapsible loop through the axial passage in the distal-to-proximal direction.

22. The method of claim 15, further comprising, prior to threading the one or more first threads through the first collapsible loop, forming the axial passage in the human body such that the axial passage forms a pathway through a bodily lumen or a bone tunnel.

* * * * *